United States Patent [19]

Polansky

[11] Patent Number: 4,576,937

[45] Date of Patent: Mar. 18, 1986

[54] 7-D-MANDELAMIDO-3(1-SULFOMETHYL-TETRAZOL-5-YL)THIOMETHYL-3-CEPHEM-4-CARBOXYLIC ACID MONOSODIUM SALT

[75] Inventor: Theodore J. Polansky, Harleysville, Pa.

[73] Assignee: SmithKline Beckman Corporation, Philadelphia, Pa.

[21] Appl. No.: 584,590

[22] Filed: Feb. 29, 1984

[51] Int. Cl.[4] ............... C07D 501/48; A61K 31/545
[52] U.S. Cl. .................................... 514/204; 544/26; 544/21
[58] Field of Search .................... 544/26, 27, 25; 424/246; 514/204

[56] References Cited

U.S. PATENT DOCUMENTS

| | | | |
|---|---|---|---|
| 3,376,310 | 4/1968 | Abbott et al. | 260/308 |
| 3,516,997 | 6/1970 | Takano et al. | 260/243 |
| 3,819,623 | 6/1974 | Takano et al. | 260/24 BC |
| 4,048,311 | 9/1977 | Berges | 546/26 |

FOREIGN PATENT DOCUMENTS

| | | |
|---|---|---|
| 818209 | 11/1974 | Belgium . |
| 823861 | 6/1975 | Belgium . |
| 2512284 | 10/1975 | Fed. Rep. of Germany . |
| 2514322 | 10/1975 | Fed. Rep. of Germany . |
| 47-0550 | 2/1972 | Japan . |
| 6916151 | 4/1971 | Netherlands . |

*Primary Examiner*—Nicholas S. Rizzo
*Attorney, Agent, or Firm*—Janice E. Williams; Alan D. Lourie; Richard D. Foggio

[57] ABSTRACT

A new cephalosporin compound, 7-D-mandelamido-3-(1-sulfomethyltetrazol-5-yl) thiomethyl-3-cephem-4-carboxylic acid monosodium salt, having unique antibacterial activity and advantageously high stability, is disclosed. Pharmaceutical compositions comprising the new cephalosporin monosodium salt are also disclosed.

16 Claims, No Drawings

7-D-MANDELAMIDO-3(1-SULFOMETHYLTET-RAZOL-5-YL)THIOMETHYL-3-CEPHEM-4-CARBOXYLIC ACID MONOSODIUM SALT

This invention relates to a new cephalosporin compound, 7-D-mandelamido-3-(1-sulfomethyltetrazol-5-yl)-thiomethyl-3-cephem-4-carboxylic acid monosodium salt, and hydrates and solvates thereof, which is represented by the following structural formula:

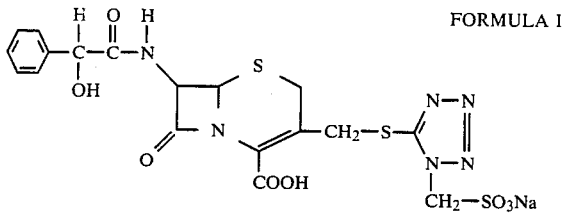

FORMULA I

The compound of Formula I has unique antibacterial activity when administered parenterally. The invention also comprises pharmaceutical compositions for treating bacterial infections containing the compound of Formula I.

The compound of Formula I is also known as SK&F 75073-Z, cefonicid monosodium salt and "Monocid" monosodium salt. A New Drug Application for cefonicid disodium salt (—COONa at the 4-position) is currently pending before the United States Food and Drug Administration.

The compound of Formula I is included within the large generic class of compounds disclosed and claimed in U.S. Pat. No. 4,048,311. Specifically, see Formula I (column 1, lines 21–58) where $R^1$ is hydrogen, n is one, $R^2$ is hydroxy, $R^3$ is

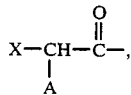

X is phenyl and A is OH. These compounds are described as existing in either the free acid form or as a "non-toxic pharmaceutically acceptable salt thereof" (line 58). At column 2, lines 66–67, the compound 7-D-mandelamido-3-(1-sulfomethyltetrazol-5-ylthiomethyl)-3-cephem-4-carboxylic acid is identified as an example of the invention. Example 1 (column 11, line 25 to column 12, line 6) relates to preparation of 7-D-mandelamido-3-(1-sulfomethyltetrazol-5-ylthiomethyl)-3-cephem-4-carboxylic acid, which is isolated and analyzed as its disodium salt. In addition, 7-mandelamido-3-(1-sulfomethyl-tetrazol-5-ylthiomethyl)-3-cephem-4-carboxylic acid is claimed as the free acid or an unspecified "pharmaceutically acceptable" salt in claims 1, 2, 4, 6, 8, 9, 10 and 12. 7-Mandelamido-3-(1-sulfomethyltetrazol-5-ylthiomethyl)-3-cephem-4-carboxylic acid disodium salt is claimed in claim 29. 7-D-Mandelamido-3-(1-sulfomethyltetrazol-5-ylthiomethyl)-3-cephem-4-carboxylic acid is claimed in claim 30.

The antibacterial activity of 7-D-mandelamido-3-(1-sulfomethyltetrazol-5-yl)thiomethyl-3-cephem-4-carboxylic acid is fully described in U.S. Pat. No. 4,048,311 (see column 6, line 19 to column 9, line 41 and the data for Compound I in Tables 1 and 2). Of particular note are the exceptionally and advantageously high blood serum levels and half lives achieved, which permit administration of the antibacterial agent on a one dose per day basis.

It has now unexpectedly been found that the newly prepared monosodium salt of 7-D-mandelamido-3-(1-sulfomethyltetrazol-5-yl)thiomethyl-3-cephem-4-carboxylic acid is a highly stable form of the antibiotic, while retaining advantageous antibacterial activity. As compared to the disodium salt, the monosodium salt exhibits a significantly higher degree and longer duration of stability at elevated temperatures. Thus, the antibiotic in its monosodium salt form can be stored for prolonged periods of time without the need for refrigeration or special handling. Due to this enhanced stability, the compound of Formula I is advantageous from a commercial viewpoint.

Comparative physical and chemical stability data for 7-D-mandelamido-3-(1-sulfomethyltetrazol-5-ylthiomethyl)-3-cephem-4-carboxylic acid disodium salt and monosodium salt appears in Table 1, below. Stability data for 7-D-mandelamido-3-(1-sulfomethyltetrazol-5-yl)thiomethyl-3-cephem-4-carboxylic acid monosodium salt at various temperatures and for various periods of time appears in Table 2, below. Lyophilized vials, 10 ml capacity, each containing 0.5 gm of the cephalosporin were used in the stability studies; reconstitution was achieved with 2.0 ml of sterile water.

TABLE 1

"COMPARATIVE STABILITY BETWEEN 7-D-MANDELAMIDO-3-(1-SULFO-METHYLTET-RAZOL-5-YL)THIOMETHYL-3-CEPHEM-4-CARBOXYLIC ACID MONO- AND DISODIUM SALTS AT 50° C."

| TIME (Weeks) | PURITY ASSAY | TOTAL ORGANIC MATERIAL IMPURITIES | WATER CONTENT | CLARITY UPON RECONSTITUTION |
|---|---|---|---|---|
| Monosodium Salt (Formula 1): | | | | |
| 0 | 94.4% | 3.1% | 2.1% | clear |
| 1 | 92.3% | 3.3% | 2.2% | clear |
| 2 | 90.2% | 3.2% | 1.9% | clear |
| 3 | 90.1% | 3.1% | 2.0% | clear |
| 4 | 92.6% | 3.2% | 1.5% | clear |
| 5 | 91.7% | 3.2% | 1.5% | clear |
| 6 | 89.5% | 3.4% | 2.7% | clear |
| 7 | 86.9% | 3.7% | 1.7% | clear |
| 8 | 92.6% | 3.6% | 1.4% | clear |
| 9 | 91.1% | 3.7% | 1.6% | clear |
| 10 | 91.1% | 4.0% | 1.3% | clear |
| Disodium Salt: | | | | |
| 0 | 93.3% | 3.1% | 2.3% | clear |
| 1 | 91.4% | 5.8% | 2.9% | cloudy (after 3 days) |
| 2 | 89.5% | 7.2% | 2.4% | cloudy |

TABLE 1-continued
"COMPARATIVE STABILITY BETWEEN 7-D-MANDELAMIDO-3-(1-SULFO-METHYLTET-RAZOL-5-YL)THIOMETHYL-3-CEPHEM-4-CARBOXYLIC ACID MONO- AND DISODIUM SALTS AT 50° C."

| TIME (Weeks) | PURITY ASSAY | TOTAL ORGANIC MATERIAL IMPURITIES | WATER CONTENT | CLARITY UPON RECONSTITUTION |
| --- | --- | --- | --- | --- |
| 3 | 86.7% | 7.2% | 2.0% | cloudy |
| 4 | 90.0% | 7.9% | 2.3% | cloudy |
| 5 | 85.6% | 8.3% | 2.1% | cloudy |
| 6 | 86.3% | 8.5% | 3.1% | cloudy |
| 7 | 81.1% | 8.9% | 1.7% | cloudy |
| 8 | 82.9% | 9.8% | 2.0% | cloudy |
| 9 | 83.5% | 10.2% | 2.1% | cloudy |
| 10 | 83.4% | 10.4% | 1.9% | cloudy |

TABLE 2
"STABILITY OF 7-D-MANDELAMIDO-3-(1-SULFOMETHYL-TETRAZOL-5-YL)-THIOMETHYL-3-CEPHEM-4-CARBOXYLIC ACID MONOSODIUM SALT AT VARIOUS TEMPERATURES AND TIMES"

| TIME (Weeks) | TEMPERATURE | DRY APPEARANCE | pH | IMPURITIES* | WATER CONTENT |
| --- | --- | --- | --- | --- | --- |
| 0 | — | white | 2.1 | 3.0% | 0.8% |
| 1 | 50° C. | white | 2.1 | — | 1.8% |
| 1 | 60° C. | white | 2.2 | 3.5% | 1.4% |
| 1 | 85° C. | yellow | 2.2 | — | 1.3% |
| 2 | 50° C. | white | 2.2 | 3.4% | 2.0% |
| 2 | 60° C. | white | 2.2 | 4.0% | 1.7% |
| 4 | 40° C. | white | 2.2 | 2.7% | 1.7% |
| 4 | 50° C. | white | 2.2 | 3.4% | 1.7% |
| 8 | 40° C. | — | 2.4 | — | 0.5% |
| 8 | 50° C. | — | — | — | 1.4% |
| 12 | ambient | — | 2.3 | 3.4% | 1.4% |
| 12 | 40° C. | — | 2.3 | 3.6% | 1.4% |
| 24 | ambient | — | 2.3 | 4.1% | 3.2% |

*(tetrazole and other cephalosporin materials)

From an analysis of the data presented in Table 1, it is apparent that 7-D-mandelamido-3-(1-sulfomethyltetrazol-5-yl)thiomethyl-3-cephem-4-carboxylic acid monosodium salt resists decomposition and clouding upon reconstitution to a significantly greater degree than the disodium salt. For example, after ten weeks at 50° C., the monosodium salt is of approximately the same purity as the disodium salt after only a few days (less than one week). In addition, as evidenced by the data presented in Table 2, 7-D-mandelamido-3-(1-sulfomethyltetrazol-5-yl)thiomethyl-3-cephem-4-carboxylic acid monosodium salt remains stable up to six (6) months at ambient temperatures.

The compound of Formula 1 is prepared by treating an aqueous solution of 7-D-mandelamido-3-(1-sulfomethyltetrazol-5-yl)thiomethyl-3-cephem-4-carboxylic acid disodium salt with an acidic cation exchange resin or with an acid of greater strength than the 4-carboxylic acid function of the starting material. When an acidic cation exchange resin is employed, a slurry is preferably used if the resin is a strongly acidic one, while a column is preferably used if the resin is a weakly acidic one. Sulfonated polystyrene resins, such as Amberlite IR-120(H), are preferred. When an acid is used to effect the conversion, hydrochloric acid, sulfuric acid or trifluoroacetic acid is preferred.

Alternatively, the compound of Formula I is prepared by titration of 7-D-mandelamido-3-(1-sulfomethyltetrazol-5-yl)thiomethyl-3-cephem-4-carboxylic acid with a stoichiometric amount of a suitable sodium-containing base such as sodium carbonate, sodium bicarbonate or sodium hydroxide.

Yet another way in which the compound of Formula I can be prepared is by treatment of a 7-D-(OH-protected mandelamido)-3-(1-sulfomethyltetrazol-5-yl)thiomethyl-3-cephem-4-carboxylic acid monosodium salt (—COOH at position 4) such as, for example, 7-(Dα-formyloxyphenylacetamido)-3-(1-sulfomethyltetrazol-5-yl)thiomethyl-3-cephem-4-carboxylic acid monosodium salt with a dilute acid such as, for example, dilute hydrochloric acid.

The compound of Formula I may exist in a hydrated or solvated form. Any and all such hydrates and solvates are included with the scope of this invention.

Pharmaceutical compositions having antibacterial activity which comprises a pharmaceutical carrier containing an active but non-toxic quantity of the compound of Formula I are also objects of this invention. The administration may be by parenteral injection such as subcutaneously, intramuscularly or intravenously. The injection of suitably prepared sterile solutions or suspensions containing an effective, non-toxic amount of the compound of Formula I is the preferred route of administration. Aqueous-based pharmaceutical compositions are preferred.

The compound of Formula I is formulated and administered in the same manner as other injectable cephalosporins. The dosage regimen comprises administration, preferably by injection, of an active but nontoxic quantity of the compound of Formula I selected from the dosage unit range of from about 100 to about 1000 mg. with the total daily dosage regimen being from about 400 mg. to about 6 g. The anticipated adult daily dosage regimen will be about from 500 mg to about 2 g., preferably about 1 g. The precise dosages are dependent upon the age and weight of the subject and on the infection being treated and can be determined by those skilled in the art.

EXAMPLE 1

Preparation of 7-D-mandelamido-3-(1-sulfomethyltetrazol-5-yl)thiomethyl-3-cephem-4-carboxylic acid monosodium salt 7-D-Mandelamido-3-(1-sulfomethyltetrazol-5-yl)thiomethyl-3-cephem-4-carboxylic acid disodium salt (1.0 g) was dissolved in 20 ml of sterile water. The solution was adjusted to pH 2.0 by addition of Amberlite IR-120H resin (less than 1.0 ml), which had been prewashed with sterile water. The resin was filtered off and the filtrate was lyophilized overnight to give the title compound.

| $C_{18}H_{17}N_6O_8S_3 \cdot Na$ | |
| --- | --- |
| Calculated | Found |
| 38.27% C | 37.33% C |
| 3.04% H | 3.26% H |

-continued

| $C_{18}H_{17}N_6O_8S_3 \cdot Na$ | |
|---|---|
| Calculated | Found |
| 14.89% N | 14.84% N |
| 22.68% O | 23.99% O |
| 17.04% S | 16.79% S |
| 4.07% Na | 3.97% Na |

EXAMPLE 2

Preparation of a pharmaceutical composition comprising 7-D-mandelamido-3-(1-sulfomethyltetrazol-5-yl)thiomethyl-3-cephem-4-carboxy-lic acid monosodium salt An injectable pharmaceutical composition is formed by adding sterile water or sterile saline solution (ca. 2 ml) to 1 g of 7-D-mandelamido-3-(1-sulfomethyltetrazol-5-yl)thiomethyl-3-cephem-4-carboxylic acid monosodium salt.

What is claimed is:

1. 7-D-Mandelamido-3-(1-sulfomethyltetrazol-5-yl)-thiomethyl-3-cephem-4-carboxylic acid monosodium salt, and hydrates and solvates thereof.

2. 7-D-Mandelamido-3-(1-sulfomethyltetrazol-5-yl)thiomethyl-3-cephem-4-carboxylic acid monosodium salt.

3. A compound of claim 1 in lyophilized form, suitable for reconstitution in an aqueous medium.

4. A compound of claim 2 in lyophilized form, suitable for reconstitution in an aqueous medium.

5. An antibacterial composition comprising a compound of claim 1.

6. An antibacterial composition comprising the compound of claim 2.

7. An antibacterial composition of claim 5 wherein such composition is an aqueous composition.

8. The antibacterial composition of claim 6 wherein such composition is a aqueous composition.

9. An aqueous antibacterial composition comprising from about 100 mg to about 1000 mg of a compound of claim 1.

10. An aqueous antibacterial composition comprising about 1000 mg of a compound of claim 1.

11. An aqueous antibacterial composition comprising from about 100 mg to about 1000 mg of the compound of claim 2.

12. An aqueous antibacterial composition comprising about 1000 mg of the compound of claim 2.

13. A reconstituted aqueous antibacterial composition comprising a compound of claim 1.

14. A reconstituted aqueous antibacterial composition comprising a compound of claim 2.

15. A method of treating bacterial infections comprising administering internally by injection to an infected or susceptible warm blooded animal an antibacterially effective but non-toxic dose of a compound as claimed in claim 1.

16. A method as claimed in claim 15, in which the compound is 7-D-mandelamido-3-(1-sulfomethyltetrazol-5-yl)thiomethyl-3-cephem-4-carboxylic acid monosodium salt.

* * * * *